US006326136B1

(12) United States Patent
Lazar et al.

(10) Patent No.: US 6,326,136 B1
(45) Date of Patent: *Dec. 4, 2001

(54) MACROMOLECULAR CONJUGATE MADE USING UNSATURATED ALDEHYDES

(75) Inventors: James G. Lazar, Bethesda; Floyd E. Taub, Silver Spring, both of MD (US)

(73) Assignee: Digene Corporation, Beltsville, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/372,810

(22) Filed: Dec. 23, 1994

Related U.S. Application Data

(63) Continuation of application No. 08/095,091, filed on Jul. 20, 1993, now abandoned, which is a continuation of application No. 07/843,806, filed on Feb. 28, 1992, now abandoned, which is a continuation-in-part of application No. 07/549,244, filed on Jul. 9, 1990, now abandoned, which is a continuation of application No. 07/176,761, filed on Apr. 1, 1988, now abandoned.

(51) Int. Cl.⁷ ..................................... C12Q 1/70
(52) U.S. Cl. .................. 435/5; 435/6; 435/7.9; 435/7.91; 435/7.92; 435/7.93; 435/7.94; 435/7.95; 435/972; 436/531; 436/536; 530/402; 530/403; 536/104; 935/77; 935/78
(58) Field of Search ............ 435/5, 6, 7.9–7.95, 435/180, 810, 972; 436/531, 536, 808; 935/77.78; 536/104; 530/350, 402, 403

(56) References Cited

U.S. PATENT DOCUMENTS

| | | | |
|---|---|---|---|
| 3,817,837 | 6/1974 | Rubenstein | 195/103.5 R |
| 3,951,748 | 4/1976 | Devlin | 195/103.5 R |
| 4,002,532 | 1/1977 | Weltman | 195/103.5 R |
| 4,166,105 | * 8/1979 | Hirschfeld | 424/8 |
| 4,225,784 | 9/1980 | Barrett | 250/303 |
| 4,235,759 | 11/1980 | Ohbu | 252/545 |
| 4,241,177 | 12/1980 | Singh | 435/7 |
| 4,267,234 | * 5/1981 | Rembaum | 428/403 |
| 4,298,685 | 11/1981 | Parikh et al. | 435/7 |
| 4,302,534 | 11/1981 | Halmann et al. | 435/6 |
| 4,311,618 | 1/1982 | Schafer-Burkhara | 252/542 |
| 4,369,226 | * 1/1983 | Rembaum | 428/334 |
| 4,378,428 | * 3/1983 | Farina et al. | 435/7 |
| 4,427,782 | * 1/1984 | Caldwell | 436/542 |
| 4,454,060 | * 6/1984 | Lai et al. | 252/547 |
| 4,469,797 | * 9/1984 | Albarella | 436/536 |
| 4,486,534 | * 12/1984 | Albert | 435/188 |
| 4,556,643 | * 12/1985 | Paau et al. | 436/501 |
| 4,563,417 | * 1/1986 | Albarella | 435/6 |
| 4,581,333 | * 4/1986 | Kourilksy et al. | 435/6 |
| 4,582,789 | * 4/1986 | Sheldon | 435/6 |
| 4,587,044 | * 5/1986 | Miller et al. | 530/211 |
| 4,687,732 | 8/1987 | Ward et al. | 435/6 |
| 4,690,906 | * 9/1987 | Duheille et al. | 436/512 |
| 4,699,876 | 10/1987 | Libeskind | 435/5 |
| 4,707,352 | 11/1987 | Stavrianpoulos | 424/1.1 |
| 4,707,440 | 11/1987 | Stavrianpoulos | 435/6 |
| 4,711,955 | 12/1987 | Ward et al. | 536/29 |
| 4,719,176 | 1/1988 | Klotz | 435/6 |
| 4,732,811 | 3/1988 | Margel | 428/403 |
| 4,777,129 | 10/1988 | Dattagupta et al. | 435/6 |
| 4,873,187 | * 10/1989 | Taub | 435/5 |

FOREIGN PATENT DOCUMENTS

| | | |
|---|---|---|
| 131830 | 1/1985 | (EP) . |
| 133473 | 2/1985 | (EP) . |
| 138357 | 4/1985 | (EP) . |
| 146 815 | 7/1985 | (EP) . |
| 151001 | * 8/1985 | (EP) . |
| 164876 | * 12/1985 | (EP) . |
| 259186 | * 3/1988 | (EP) . |
| 263184 | * 4/1988 | (EP) . |
| 560013511 | 1/1981 | (JP) . |
| WO 85/05685 | 12/1985 | (WO) . |
| 8909404 | * 5/1989 | (WO) . |
| WO 89/09404 | 10/1989 | (WO) . |

OTHER PUBLICATIONS

Chemical Abstract 112:104792. "Formulation & Characterization of Polyglutaraldehyde Nanoparticles . . . ".*
Margel, "Polyaldehyde Microspheres as Probes for Cell Membranes" *Ind. Eng. Chem. Prod. Res. Dev.*, vol. 21, pp. 343–348 (1982).*
Renz et al "A Colorimetric Method for DNA Hybridization" *Nucleic Acids Research*, vol. 12 No. 8 (1984) pp. 3435–3444.*
Hung, C.T., et al., "Formulation and Characterization of Magnetic Polyglutaraldehyde Nanoparticles as Carriers for Poly–(1–Lysine)–Methotrexate," Chemical Abstract 112:104792g, *Drug Dev. Ind. Pharm.*, 16(3), pp. 509–521 (1990).*
Margel, S., "Polyaldehyde Microspheres as Probes for Cell Membranes," Ind. Eng. Chem. Prod. Res. Dev., vol. 21, pp. 343–348 (1982).*
Place, et al., "The Fixation of Anti–$HB_sAg$ on Plastic Surfaces," J. Immunol. Met., vol. 48, pp. 251–260 (1982).*
Angles–Cano, F., et al., "A Solid Phase Immunoassay for the Specific Detection of Monoclonal Antibodies Against Different Epitopic Determinants of Tissue–Plasminogen Activators," *J. Immunol. Methods*, pp. 115–127 (1984).
Borel, et al., "Conjugation of DNA Fragments to Protein Carriers by Glutaraldehyde: Immunological methods," J. Immunol. Met., vol. 67, pp. 289–302 (1984).
Grunstein, et al., Proc. Natl. Acad. Sci. USA, vol. 72, p. 3961 (1975), "Colony hybridization: A method for the isolation of cloned DNAs that contain a specific gene".

(List continued on next page.)

*Polysciences, Inc.*, Aug. 1986, Data Sheet #124.

Primary Examiner—Carol A. Spiegel

(57) ABSTRACT

Conjugate probes are prepared in a one step process by incubating a macromolecule and a labeling group with an unsaturated polyaldehyde as the conjugating agent. The conjugating agent is capable of bonding virtually any labeling group to a macromolecule. Conjugate probes have been shown to have a high degree of specificity and exhibit a strong signal with minimal background.

31 Claims, No Drawings

OTHER PUBLICATIONS

Rembaum, et al., "Polyglutaraldehyde: A New Reagent for Coupling Proteins to Microspheres and for Labeling Cell-Surface Receptors," *Journal of Immunological Methods*, vol. 24, pp. 239–254 (1978).

Renz, M., "Polynucleotide–histone HI Complexes as Probes for Blot Hybridization," Eur. Mol. Biol. Organ. J., vol. 2, pp. 817 (1983).

Renz, M., et al., "A Colorimetric Method for DNA Hybridization," *Nucleic Acids Research*, vol. 12, No. 8, pp. 3435–3444 (1984).

Southern, *J. Mol. Biol.*, vol. 98, p. 503 (1975), "Detection of Specific Sequences Among DNA Fragments Separated by Gel Electrophoresis".

* cited by examiner

MACROMOLECULAR CONJUGATE MADE USING UNSATURATED ALDEHYDES

This is a continuation of U.S. Ser. No. 08/095,091 filed Jul. 20, 1993, now abandoned, which is a continuation of U.S. Ser. No. 07/843,806 filed on Feb. 28, 1992, now abandoned, which is a continuation-in-part of U.S. Ser. No. 07/549,244 filed Jul. 9, 1990, now abandoned, which is a continuation of U.S. Ser. No. 07/176,761, filed Apr. 1, 1988, now abandoned, by Floyd E. Taub, Kelly K. Rosito and Thomas W. Higgs.

BACKGROUND OF THE INVENTION

This invention relates to macromolecular conjugates, such as nucleic acid hybridization probes and immunological probes, useful as research and diagnostic tools. More particularly, it relates to making macromolecular conjugates by employing a universal conjugating agent.

Probe technology is emerging as a powerful tool in diagnostic testing, detection of genetic defects and the mapping of prokaryotic and eukaryotic genomes. Nucleic acids are characteristic of and therefore may be used to indicate the presence of a particular genus or species of bacteria or type of virus. They may indicate the presence of genes for pathogenicity or for antibiotic resistance or for a particular genetic disease.

Nucleic acid hybridization probes are well known tools of molecular biology. Grunstein et al., *Proc. Natl. Acad. Sci. USA* 72:3961 (1975) and Southern, *J. Mol. Biol.* 98:503 (1975), describe hybridization techniques using radiolabeled nucleic acid probes.

Diagnostic tests based on culture techniques are often difficult and slow to produce results. Many pathogens, including viruses and bacteria, require incubation from overnight to six weeks to yield diagnostic results. In addition, some organisms cannot be cultured.

Monoclonal antibody techniques often have limited specificity. They are subject to undesirable cross reactions and the inability to detect antigenic variants. Nucleic acid hybridization probes have the advantages over other methods of speed and high specificity. However, existing hybridization techniques which utilize radioisotopes introduce additional expenses in disposal of radioactive waste products and monitoring personnel and the work place for contamination. Autoradiographic detection may require up to two weeks of exposure. These techniques are not suited to commercial areas such as clinical diagnosis.

One technique under development to overcome the drawbacks inherent in radioisotopic probes is the non-radioactive labeling of nucleic acids. Any labeling group that does not prevent hybridization of the nucleic acid with its target may be used to form a probe. After hybridization with a target nucleic acid, the labeled duplex is reacted with additional reagents to provide a signal. The most common method of indirect labeling is to attach biotin, a small vitamin, to the nucleic acid, using chemical or enzymatic techniques. Following hybridization, the biotin is detected with avidin, an egg white protein. Avidin may be labeled with an enzyme or a fluorochrome. Enzyme labels are detected by a calorimetric reaction. Fluorochrome labels are detected by illumination with light of a specific wavelength.

The ability of biotin to bind to avidin has been exploited in hybridization assays. U.S. Pat. No. 4,581,333 to Kourilsky, et al., for example, discloses the use of avidin-bound enzymes to detect hybridization between biotinylated DNA probes and a particular nucleic acid molecule of interest. European Patent Application 133,473 discloses the use of biotin-avidin bridging agents as well as sugar-binding lectins to link the proteins and nucleic acid molecules used in a hybridization assay.

Avidin-biotin techniques are complex because of the many steps involved: probe is labeled with biotin, avidin is labeled with an enzyme or fluorochrome, the biotinylated probe is, hybridized to the target, and the labeled avidin is reacted with the biotinylated probe, the labeled avidin is detected by a colorimetric reaction or by illumination with light. A method of attaching a signal-generating enzyme or fluorochrome directly to the DNA to make a probe would be advantageous because the diagnostic test would be greatly simplified: the DNA would be labeled with the enzyme or fluorochrome, hybridized to the target, and detected by a colorimetric reaction or by illumination with light.

Antibodies have been employed as bifunctional conjugating agents to link proteins to nucleic acid molecules. U.S. Pat. No. 4,556,643 to Paau et al. discloses the use of antibodies, as well as DNA binding proteins, in hybridization assays. European Patent Application 146,815 discloses hybridization assays which employ antibodies capable of binding to a DNA intercalator molecule. Similar inventions are disclosed in U.S. Pat. No. 4,582,789 to Sheldon and in European Patent Application 131,830. These methods also require complex assay systems as compared to a directly labeled DNA probe.

A large number of covalent conjugating agents are known in the immunoassay art, where they have been used to directly attach such labels to antibodies or antigens. Antibodies or antigens labeled in this manner are sometimes referred to as immunologized probes. Such agents are also often used to attach immunogens to carriers. U.S. Pat. No. 4,469,797 to Albarella, discloses digoxigenin derivatives capable of acting as bifunctional coupling agents to link immunoglobulins to polypeptide carriers. U.S. Pat. No. 4,378,428 to Farina et al., discloses covalent conjugating agents which may be used in a homogeneous immunoassay. U.S. Pat. No. 4,302,534 to Halmann, et al., discloses the use of either antigen or antibody labeled with peroxidase in an immunoassay. U.S. Pat. No. 3,951,748 to Devlin, discloses an immunoassay in which a coupling agent immobilizes protein molecules to an insoluble matrix. U.S. Pat. No. 3,817,837 to Rubenstein discloses an immunoassay which employs a covalent conjugating agent to bind an enzyme ligand. The use of biotin as a bifunctional conjugating agent is disclosed in U.S. Pat. No. 4,298,685 to Parikh et al. U.S. Pat. No. 4,241,177 to Singh, additionally discloses similar covalent conjugating agents.

A small number of proteins bind readily to deoxyribonucleic acid (DNA). These are referred to as DNA binding proteins. Known DNA-binding proteins such as histones, RecA and single-stranded DNA binding protein (SSB) have been employed in hybridization and diagnostic assays. European Patent Applications 183,822 and 164,876 disclose hybridization methods for identifying known genetic sequences in a target DNA molecule which employ DNA binding proteins such as *E. coli* RecA and SSB. Japanese Patent Application 56001351 discloses a method for quantitatively analyzing DNA binding protein by affinity chromatography using a carrier to which DNA is linked. Histones and some other positively charged proteins form excellent DNA binding proteins. These proteins are candidates for labeling groups. However, most proteins that are signal generating or that would react with signal molecules are not DNA binding proteins. These may be attached to nucleic acids by covalent conjugating agents. Conjugate probes are made by bonding a labeling group to a nucleic acid by using a conjugating agent.

A number of methods are known for covalently crosslinking proteins to nucleic acid molecules. European Patent Application 151,001 discloses a polynucleotide which is covalently crosslinked to a protein molecule. European Patent Application EP 138,357 discloses additional bifunctional covalent conjugating agents. U.S. Pat. No. 4,587,044 to Miller et al. discloses nucleic acids which are modified by esterification with a saturated or unsaturated aliphatic dicarboxylic acid or anhydride to produce a molecule capable of being crosslinked to a protein. U.S. Pat. No. 4,699,876 to Libeskind, discloses a number of bifunctional cross-linking agents including N-succinimidyl 4-glyoxalylbenzoate, carbonyl imidazole, dimethyl superimidate, 1-ethyl,3-dimethylaminopropylcarbodiimide, paranitropenyl 3(2-bromo,3-ketobutylsulfonyl)propionate or other active esters, glutaraldehyde and other suitable equivalent.

The use of glutaraldehyde as a covalent conjugating agent capable of binding nondetectable proteins to nucleic acid molecules is disclosed by Borel et al., *J. Immunol. Met.* 67:289–302 (1984). Borel et al. describe a 2 stage process in which an oligonucleotide is incubated with glutaraldehyde and the oligonucleotide-glutaraldehyde conjugate is then incubated with the desired protein to produce the oligonucleotide-protein conjugate. Glutaraldehyde has also been used to covalently attach histones to nucleic acids, as reported by Renz, M., *Eur. Mol. Biol. Organ. J.* 2:817 (1983). Histones are lysine rich (i.e. positively charged) DNA-binding proteins. Glutaraldehyde adds covalent bonds to these two moieties that are already matched by a natural strong affinity. The tight binding between nucleic acids and lysine rich histones allows efficient glutaraldehyde crosslinking at low concentrations.

It is not always possible to find proteins that are easily detectable and also have a strong natural affinity for nucleic acids. Proteins that do not have a natural affinity for nucleic acids will not allow the same efficient glutaraldehyde crosslinking. Therefore, one would expect varying degrees of success from attempts to crosslink a variety of proteins to nucleic acids using glutaraldehyde or any other conjugating agent.

Renz et al., *Nucleic Acid Res.* 12:3435–3444 (1984) considered ionic binding between the protein and the nucleic acid to be essential to the success of a conjugating agent which covalently binds them. To convert horseradish peroxidase into a DNA-binding protein, polyethylenimine carrying primary amino groups was fused to horseradish peroxidase with p-benzoquinone as the crosslinking agent. This modified horseradish peroxidase had an increased affinity for single stranded DNA and could be covalently conjugated with glutaraldehyde.

U.S. Pat. No. 4,166,105 to Hirschfield discusses linking a labeling group to an antibody using non-polymerized polyaldehydes such as glutaraldehyde.

U.S. Pat. No. 4,267,234 to Rembaum links biological molecules to water insoluble polyglutaraldehyde microspheres, to produce water insolubilized biomolecules.

A wide variety of cationic detergents possessing hydrophobic groups on one end and positively-charged groups on the other may be prepared. Such detergents are disclosed by, for example, U.S. Pat. No. 4,235,759 to Ohbu and U.S. Pat. No. 4,454,060 to Lai, et al. Such detergents have found use as cleaning agents such as shampoos, bubble baths and skin cleansers, etc.

Detergents were found to be DNA-protein conjugating agents, as disclosed by U.S. Pat. No. 4,873,187 to Taub.

Place et al., *J. Immunol. Met.* 48:251–260 (1982) discloses a method of improving the adsorption of protein to plastic surfaces to improve the reliability of quantitative solid phase immunoassays. Place et al. observed that antibody to hepatitis B surface antigen (anti-HBSAg) could be partially removed from a plastic surface by serum albumin. Removal could be substantially prevented if the wells of a polyvinyl chloride (PVC) microtiter plate were first treated with 2% polyglutaraldehyde. Monomeric glutaraldehyde was, in contrast, ineffective to improve the binding of protein to plastic.

It is therefore an object of the present invention to provide a new method of forming a conjugate probe formed between a macromolecule and a labeling group.

It is a further object of the present invention to provide a conjugate probe made from any macromolecule by binding to any labeling group.

It is another object of the present invention to provide hybrids and a method of making hybrids between the conjugate probe and its target nucleic acid.

It is yet another object of the present invention to provide a method of detecting the presence of a target nucleic acid by detecting the presence of a labeling group that is bound to a hybrid.

It is another object of the present invention to provide test kits for making macromolecular conjugates and for performing hybridization testing using the conjugate probe and a hybridization medium.

SUMMARY OF THE INVENTION

Conjugate probes are prepared in a one step process by incubating a macromolecule, such as a protein, nucleic acid, carbohydrate or lipid, and a labeling group with an unsaturated polyaldehyde as the conjugating agent. The conjugating agent is capable of bonding virtually any labeling group to a macromolecule. The conjugate probes have been shown to have a high degree of specificity and exhibit a strong signal with minimal background. The unsaturated polyaldehyde binds several molecules not bound by glutaraldehyde.

Several examples demonstrate preparation and advantages of the resulting conjugate probes.

DETAILED DESCRIPTION OF THE INVENTION

A conjugate probe and a method of making the probe, a hybrid between target and the probe and a method of making the hybrid, a method of detecting the presence of a target molecule by using the probe and a test kit for hybridization or binding of a specific target in a test sample, are provided. The probe is highly sensitive and produces a strong signal as a result of bonding a macromolecule to a labeling group using a polymerized aldehyde, such as polyglutaraldehyde or an unsaturated polyaldehyde.

In order to provide a clear and consistent understanding of the specification and the claims, including the scope given to such terms, the following definitions are provided:

Bifunctional Molecule: is a molecule that has two functional regions. It is capable of attracting two molecules that are similar to or different from each other. Detergents are typical examples.

Bridging Reagent: a molecule which acts as a connector between parts of a conjugate or between a conjugate and a solid substance. As used herein, it does not function as a conjugating agent.

Conjugate: a molecular species composed of two or more molecules regardless of the form of attachment. As used herein, a conjugate is comprised of a macromolecule, a labeling group and a conjugating agent.

Conjugating Agent: a molecule which forms a bond between two or more other molecules regardless of their relative attraction for each other. As used herein, a conjugating agent is a molecule which forms a stable bond between a macromolecule and a labeling group. The preferred conjugating agents are multifunctional aldehydes, such as alpha-beta unsaturated aldehydes and aryl aldehydes.

Complementary Conjugate Probe: is a probe which binds to its corresponding target. For example, a complementary nucleic acid conjugate probe hybridizes to a complementary target nucleic acid. A complementary antibody conjugate probe binds to its target antigen. A complementary receptor conjugate probe binds to its receptor target molecule.

Complementary Nucleic Acids: as referred to herein are capable of substantial base pairing throughout their length.

Detergents: are bifunctional molecules having a positively charged region and a hydrophobic region. Detergents are capable of binding to molecules of different types of non-convalent interaction and can bring together molecules which have little or no attraction for each other.

Direct Labeling: a method of labeling nucleic acids in which the labeling group is attached to the nucleic acid.

Hybridization: a process in which a nucleic acid joins with a complementary nucleic acid through base pairing. The process is sometimes referred to as reannealing.

Labeling Group: a molecule which is attached to a biological molecule as a marker. As used herein it is a molecule attached to a macromolecule in a conjugate. Labeling groups may be proteins or non-protein molecules or atoms or groups of atoms which are detectable. Among the labeling groups are radiolabeled molecules, antigens, antibodies, colored or fluorescent dyes, enzymes, chemiluminescent labels, phycobilins, ferritin, nucleic acid binding proteins and similar molecules.

Macromolecule: any large molecule having a 3-dimensional structure. As used herein, it refers to molecules such as a protein or nucleic acid which will attach to a target. It may be attached to a labeling group to form a conjugate probe. The labeling group provides feedback in the form of a detectable molecule or complex.

Nucleic Acid: a chain of nucleotide bases. As used herein, nucleic acid refers to any nucleic acid sequence, strand of nucleic acid, oligonucleotide, or polynucleotide formed from the polymerization of nucleotides or the cutting of longer chains of nucleotides. It may be DNA or RNA or any substantially similar polymer. It may be single stranded or double stranded.

Polymerized Aldehyde: An α-β unsaturated homo or hetero polymer of an aldehyde having two or more free CHO groups.

Polyglutaraldehyde: An α-β unsaturated polymer of monoglutaraldehyde having two or more sites at which it may form covalent bonds with other molecules.

Probe: a nucleic acid or other macromolecule used to detect a target, such as in molecular hybridization to detect complementary nucleic acid in the presence of a large amount of non-complementary nucleic acid or in immunoassays to detect an antigen or an antibody. As used herein, it is referred to as a conjugate probe. A conjugate probe is a probe formed by conjugation of a macromolecule to a labeling group by a conjugating agent. It is detectable by detecting the presence of the labeling group.

Signal Molecule: a compound used in the assay of affinity labels as a means of detecting the presence of the labeling group. Some signal molecules are labeling groups which can be detected with a simple assay technique. Examples of signal molecules are fluorochromes and enzymes linked to antibodies.

Substantial Sequence Homology: denotes nucleotide sequences that are related enough in sequence to strongly bind to one another under standard or stringent hybridization conditions. Nucleotide differences between such sequences having substantial sequence homology will be de minimus in affecting the hybridization of the two molecules.

Target: as used herein, the term refers to nucleic acid having sufficient nucleotide base homology with a conjugate probe nucleic acid to permit formation of stable hybrid, an antigen or antibody to which an antibody probe or antigen probe, respectively, will bind or other suitable macromolecule such as a receptor.

The conjugate probe includes at least one macromolecule, a labeling group and polymerized aldehyde, such as polyglutaraldehyde or other unsaturated polyaldehyde. The probe may initially consist only of the labelling group and polymerized aldehyde or of the macromolecule specific for a particular target and the polymerized aldehyde. The macromolecule may be a protein or a nucleic acid, or even a smaller molecular weight molecule which selectively binds to a target.

The Polymerized Aldehydes

Polymerized aldehydes useful to make the improved conjugate probe are the polymerization products of any dialdehyde of the formula (I):

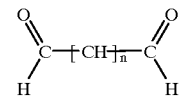

n = 1 - 18 which under acidic or basic conditions undergoes polymerization via aldol condensation to α,β unsaturated forms of formula (II) or higher forms:

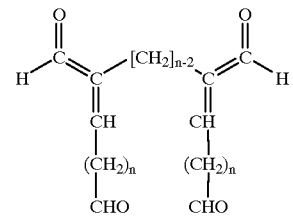

The compounds may contain two or more aryl aldehyde functional groups (formula III):

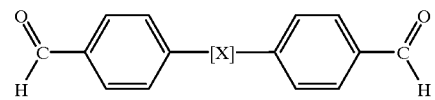

where X is a direct bond or a substituted or unsubstituted alkyl or aryl residue.

The compounds may contain one or more α-β-unsaturated aldehyde groups and one or more aryl aldehyde groups (formula IV):

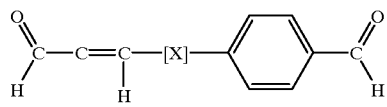

Any of the compounds of formulae (I), (III) or (IV) which may contain additional unsaturation due to the presence of additional double bonds or phenyl conjugated to the aldehyde functional group can also be used (formula V):

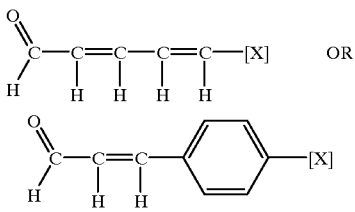

The majority of the α,β unsaturated compounds may be prepared by a base-catalyzed crossed aldol condensation between two different aldehydes. The preparation is more efficient if one of the reactants cannot undergo a self-aldol condensation, for example, formaldehyde, glyoxal, benzaldehyde, terephthaldicarboxaldehyde.

Another method of producing multi-functional α,β unsaturated aldehydes is by the Schiff base condensation of two moles of terephthaldicarboxaldehyde (TPDA) with one mole of a compound containing two amino groups. A significant advantage of this method of preparation of bifunctional unsaturated aldehydes is that the length of the product can be easily varied by the proper choice of diamino compound. Either aliphatic (scheme VI) or aromatic (scheme VII) amino compounds can be used.

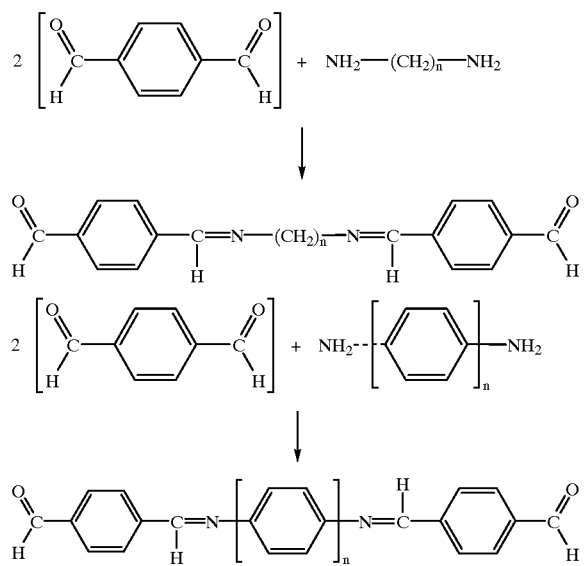

Compounds containing multiple α,β-unsaturated aldehyde functional groups may also be prepared by the polymerization of a linear dialdehyde via an acid or base catalyzed self-aldol condensation. Illustrated below is the formation of polyglutaraldehyde trimer (formula VIII):

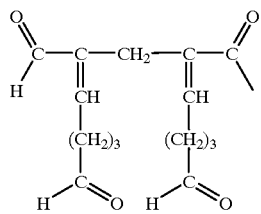

The preferred conjugating agent is water-soluble polyglutaraldehyde. Polyglutaraldehyde can be differentiated from its monomeric form by the absorbance peaks at 235 nm and 280 nm respectively. Monoglutaraldehyde is believed to undergo aldol condensation above pH 7 to form long-chained α,β-unsaturated polyglutaraldehyde. The formation of polyglutaraldehyde from glutaraldehyde is known to occur spontaneously and in fact has been reported to seriously decrease the functioning of glutaraldehyde. Glutaraldehyde is generally supplied bottled under inert gases and refrigerated to avoid polymerization during storage. The literature indicates that the polymerized contaminant of glutaraldehyde is detrimental for almost all application. For example, *PolySciences*, August 1986 Data Sheet #124 states that glutaraldehyde is subject to air oxidation and polymerization when in concentrations of 25% or more. The polymeric forms are reported by Sabatini, D. D., et al., *J. Histochem. Cytochem.* 12:57 (1967), to be poor fixatives and inhibit enzymes.

In contrast, contrary to this teaching, water-soluble polymerized aldehydes such as polyglutaraldehyde have been discovered to be superior conjugating agents and useful in probes suitable for hybridization or binding with a functional labeling group.

The most preferred polyglutaraldehyde is an aqueous solution of polyglutaraldehyde in glutaraldehyde. Aqueous solutions of glutaraldehyde are allowed to polymerize in a controlled manner by raising the pH to the range 8–12, preferably around 10, at about room temperature, for up to 48 hours or so, then acidifying to pH 2–7 particularly to around 4. Any precipitate, usually high molecular weight, water-insoluble polyglutaraldehyde, is removed and the clear supernatant is used, or stored at 4° C. until use. Ideally, the polymerized glutaraldehyde is an oligoaldehyde. The molecular weight, however, is not critical; solubility in solution is extremely important, most preferably solubility in an aqueous solution.

A good measure of polymerization product in solution is the ratio of $OD_{235}$ (polymer) to $OD_{280}$ (monomer). It is preferably higher than 1.0, most preferably higher than 10, and up to the point of insolubility.

When the polymerization is carried out at the higher ranges of pH (10–12), the solution may also show an adsorption peak at 290 nm.

Preferably the weight average molecular weight (MW) of the polyglutaraldehyde is generally less than 5,000, most preferably less than 1,000.

Unsaturated polymerized aldehydes such as polyglutaraldehyde form stable conjugates between macromolecules and labeling groups. Polyglutaraldehyde has been demonstrated to conjugate: β-phycoerythrin to phycoerythrin, horseradish peroxidase or DNA; horseradish peroxidase to horseradish peroxidase, glucose oxidase, alkaline phosphatase, avidin or DNA; DNA to glucose oxidase or alkaline phosphatase; and RNA to apoaquarin, urokinase or alcohol oxidase.

Polyadipaldehyde (poly-1,6-hexanedial), 2,4-biformyl-1,5-pentadiene (compound IX, example 14) and 3,5-biformyl- 2,6-heptadiene-1,7 dial (compound X, example 15) have also been demonstrated to conjugate DNA to horseradish peroxidase. When used in in situ hybridization, the probes prepared with these conjugating agents gave higher signals than probes prepared with commercial glutaraldehyde.

Thus, it has been found that compounds such as polyglutaraldehyde are universal conjugating agents of superior quality. They can conjugate virtually any macromolecule with any labeling group.

It has been found that compounds such as polyglutaraldehyde will form conjugates between a nucleic acid and several labeling groups. The resulting conjugate probe yields a strong signal. An example of this effect is seen in the conjugation of several horseradish peroxidase groups with a single nucleic acid using polyglutaraldehyde. Polyglutaraldehyde is shown to be a superior conjugating agent because it is able to form conjugates between DNA and proteins which monoglutaraldehyde cannot. It is also shown to be capable of forming conjugates with a stronger signal due to the presence of a relatively high number of labeling groups.

Polymerized aldehyde such as polyglutaraldehyde can be used alone or in conjunction with monomeric forms, such as monoglutaraldehyde. The combined uses of these two conjugating agents may be useful, for example, in controlling the average molecular weight of the conjugating agent or for achieving a controlled conjugation reaction.

The polymerized aldehydes of the invention are capable of covalently conjugating virtually any labeling group to any macromolecule by a simple one step incubation process. The process may however be optimized for some conjugates by complexing the polymerized aldehyde, e.g., polyglutaraldehyde or a mixture of polyglutaraldehyde and monoglutaraldehyde, to either the labeling group or the macromolecule and then incubating the resulting complex with the next member of the conjugate probe.

The Specific Macromolecule

The macromolecules may consist of two or more nucleic acid sequences if it is prepared from a mixture of different nucleic acids or if several similar or identified nucleic acids are bound to each other and the label. The molecule may be a protein, for example, an antigen, an antibody, a receptor molecule, or a molecule which binds to a receptor.

If the probe contains nucleic acid, the conjugate probe usually functions by hybridization of the macromolecule portion of the conjugate to a complementary portion of a target. If the probe contains an antibody, for example, the conjugate probe functions by binding to the appropriate antigen. The specificity of a conjugate probe requires that not only must the probe be specific to its target, but it must not be functionally inactivated by its position or chemical association with respect to other molecules forming the conjugate.

The nucleic acid molecule used in one embodiment of the conjugate probe of the present invention may be deoxyribonucleic acid (DNA) or ribonucleic acid (RNA) or a fragment of DNA or a molecule substantially similar to DNA or RNA such as methylphosphonate nucleic acid or thiolnucleic acid, or transaminated or methylated nucleic acid. The DNA or RNA is preferably single-stranded. It may be of eukaryotic, procaryotic or viral origin.

The DNA or RNA may be obtained by using restriction enzymes, chemical synthesis, or sonication. Chemically synthesized nucleic acids can be made such that they have substantial sequence homology to the desired target nucleic acid. Restriction enzymes cut nucleic acids at specific recognition sites. In the presence of a uniform pool of nucleic acids, restriction enzymes yield a uniform and predictable heterogenous group of nucleic acids. Sonication applies energy to nucleic acid to overcome chemical bonds. Sonication yields an unpredictable heterogenous group of nucleic acids. Both sonication and restriction enzymes will yield nucleic acids which are homologous to a portion of the nucleic acid from which it was derived. A pool of heterogenous nucleic acids derived from the same virus, for example, will hybridize with its complementary portion of nucleic acid from the same type of virus except where a substantial mutation has occurred. Techniques for the isolation of such nucleic acids are well known to those of ordinary skill in the art. See for example, Maniatis, T., et al. in *Molecular Cloning, A Laboratory Manual,* Cold Spring Harbor, N.Y. (1982), or Davis, R. W., et al. in *A Manual for Genetic Engineering, Advanced Bacterial Genetics,* Cold Spring Harbor, N.Y. (1980), the teachings of which are incorporated herein.

The Label

Any labeling group may be used according to the present invention if it will bind to a molecule in the presence of water-soluble polymerized aldehyde, such as polyglutaraldehyde. For example, any enzyme whose activity may be monitored, for example, by interaction with a chromogenic substrate, or by interaction with another molecule such as an antibody. Enzymes whose presence can be monitored through the use of chromogenic substrates or calorimetric reactions for in situ assays are preferred. A stable precipitate results which can easily be seen. Such enzymes include sugar hydrolyzing enzymes such as betagalactosidase, oxidase enzymes such as glucose oxidase, peroxidase enzymes such as horseradish peroxidase. Light-generating luciferase proteins can also be used in situ or in other formats.

Other labeling groups may be preferable in other formats. For example, phycobilins are photosynthetic pigments which consist of phycoerythrobilin and phycocyanobilin. They are composed of open tetrapyrroles, covalently bound to two protein molecules, that form aggregates in nature called phycobilisomes which account for the color in red algae and in cyanophytes. Phycobilins are preferred labeling groups because they do not require an enzyme assay for detection.

More than one labeling group may be present in the conjugate probe to provide a greater signal. Two or more different labeling groups may be desired for a particular type of assay. Therefore, the labeling groups may be the same or different.

Formation of the Conjugate Probe

As used herein, the reaction of the polymerized aldehyde, e.g., polyglutaraldehyde, with one component of the probe is termed activating the components. Labeling density is achieved by manipulating the mass ratio of labeling group to macromolecule and the concentration of polymerized aldehyde in the mixture.

The mass ratio of the labeling group to macromolecule in the incubation mixture determines the amount of signal that will be detectable from a hybrid. Although mass ratio of 1:2, labeling group to molecule is detectable, a mass ratio from 2:1 to 15:1 is preferred. Mass ratios from 4:1 to 8:1 are especially preferred. The highest readable signal is obtained at these ratios. The preferred ratio may vary for different signal generators and different assay methods.

Detergents are bifunctional molecules having a positively charged region and a hydrophobic region. They will bind to both nucleic acid and protein by non-covalent interaction. It has now been found that when a detergent is incubated with the substrates to be conjugated, covalent conjugation by polymerized aldehyde is improved.

Polymerized aldehyde may be used in conjunction with a bridging reagent. The bridging reagent may attach to polymerized aldehyde which then attaches a macromolecule and a label. For example, a conjugate of the sequence macromolecule-polyglutaraldehyde-bridging reagent-polyglutaraldehyde-label may be formed. A sequence may also be formed in which the bridging reagent binds directly to either the macromolecule or the labeling group. The bridging reagent may be albumin, polylysine or any molecule with at least one group that is reactive with an $NH_2$ group and another group that is reactive with a labeling group. The bridging reagent may be used in conjunction with any solid support such as a filter, a column or a microtiter plate. Molecules may also be directly attached to solid supports via unsaturated aldehydes.

Hybrid Formation

Hybrids are made by allowing the macromolecule of the conjugate probe to pair with its target. This may be done in a variety of ways. The target macromolecule may be bound to a solid support such as an affinity column. The conjugate probe is allowed to pass across the column and bind with its target. A viral, body fluid, tissue, or cell sample suspected of containing target nucleic acid or protein may be placed on an inert solid support. In some cases it may be desirable to amplify the sample in culture or in a chemical reaction before applying a conjugate probe. If necessary, the sample is then treated with a reagent effective in opening viral capsids, cells and tissues and denaturing the nucleic acid. This may be done before, during, or after the sample is fixed to an inert solid support. Several reagents, such as alcohols, amides, ureas, phenols, sulfoxides, may be used to denature nucleic acid.

Sandwich hybridization may be performed by hybridizing a chemically biotinylated DNA probe to a conjugate probe having homologous DNA conjugated by polyglutaraldehyde. The hybrids can be isolated by reacting them with avidin that is immobilized on a microtiter well. Another form of sandwich hybridization is performed by hybridizing a chemically biotinylated DNA probe and a non-homologous conjugate probe made using polymerized aldehyde to target DNA that will hybridize to both probes. The hybrids can be isolated by reacting the hybridization mixture with immobilized avidin. These and other methods of preparing samples will occur to one of ordinary skill in the art. Sandwich hybridization of antigens and antibodies are also well known.

Hybridization occurs easily in fixed samples in which the nucleic acid has been denatured. The sample is reacted with a conjugate probe. Nucleic acid of the conjugate probe is allowed sufficient time to locate and hybridize to its target. Usually 10 minutes to two hours are allowed. Non-hybridized conjugate probe is washed from the sample. A concentration of from 0.1 $\mu$g/ml to 50 $\mu$g/ml, preferably 0.3 to 30.0 $\mu$g/ml, of conjugate probe is used when applying it to a fixed sample of denatured nucleic acid.

Signal to Background Ratio

A high signal to background ratio is most preferred. An ideal conjugate probe gives a strong signal without background. However, low levels of background are easily tolerable in the presence of a strong signal. For example, conjugate probes at a concentration of 2.5 $\mu$g/ml were applied to samples containing target. The signal and background were measured as the mass ratio of horseradish peroxidase to DNA in a conjugate probe increases from 1:2 to 8:1. Two effects are evident. The amount of signal increased until the mass ratio reached 4:1 or 8:1 but did not further increase as the mass ratio of protein to DNA increased above 8:1. The level of background remained at zero until the mass ratio reached 4:1 and increased above zero as the ratio increased above 4:1.

Signal Intensity

The concentration of reagents in the conjugation mixture can determine the signal intensity that arises from a hybridized conjugate probe. A final concentration of reagents greater than 0.10 mg/ml in conjugate probe mixtures having a ratio of labeling group to macromolecule, such as nucleic acid, mass ratio of 4:1 and a polymerized aldehyde concentration of 2.5%, is preferred. A concentration of reagents greater than 0.25 mg/ml is especially preferred.

Specificity

Extent and specificity of nucleic acid hybridization is affected by a number of factors. For example, a covalent bond between the conjugating agent and a nucleic acid or between the nucleic acid and a labeling group can alter the specificity of the nucleic acid for its target. The purity of the nucleic acid preparation in the conjugate probe affects specificity. The thermal stability of the probe nucleic acid is increased in proportion to the relative number of G-C units present. Specificity can be reduced by breakdown of the nucleic acid at high temperatures. Hybridization typically proceeds at temperatures between 37 and 70° C.

Specificity decreases as the length of the nucleic acid decreases. Little or no specificity can be assigned to hybridizations involving short nucleic acids (below 12 nucleotides). Nucleic acids having 20 or more bases are preferred. The ionic strength of the hybridization solution affects the rate of hybridization and also the thermal stability of resulting hybrids. Conjugate probe concentration should be in excess of target concentration, preferably about 100 fold or more, to promote hybridization. Incubation time must be sufficient to allow sufficient hybridization for detection. Volume exclusion reagents such as dextrin effectively increase the concentration of the conjugate probe, thereby increasing the rate of hybridization. Conjugate probes made with polyglutaraldehyde have been found to exhibit 100% specificity for target nucleic acid by hybridizing to target nucleic acid and failing to hybridize to non-target nucleic acid in every case tested. They may show greater sequence specificity at a given temperature than non-conjugated probes. The specificity of nucleic acid in a conjugate probe for its target should not be abolished by the chemical bonds formed during conjugation.

Target nucleic acid is detected by detecting the presence of the labeling group on the conjugate probe. After hybridization, a washing step removes any conjugate probe that is not hybridized. A labeling group is usually detected by its reaction with a signal molecule. Among the variety of detection means are spectroscopic, photochemical, immunochemical, biochemical, chemical, fluorescence, luminescence and isotopic. A labeling group may be detected directly. Directly detectable labeling groups include, for example, radioisotopes, fluorochromes and phycobilins. It is preferred not to use a radioisotope in order to avoid the need to dispose of radioactive wastes. A labeling group may be detected indirectly as a result of a chemical reaction which forms a detectable product. For example, an enzyme might react with a signal molecule to form a detectable precipitate. Examples of signal molecules are enzyme substrates, chromogens and prechromogens.

The conjugate probe can be distributed as part of a test kit for detecting the presence of target macromolecule in a sample. By the term "kit" is meant a packaged combination of one or more containers, devices or the like holding the necessary reagent elements for detecting the presence of at least one target macromolecule. It usually includes written instructions for performing assays. In all cases, the kit must contain one or more conjugate probes according to the number of targets sought and the format of the assay. (The sandwich format assay requires more than one conjugate probe). The labeling group may be the same or different for each conjugate probe.

The kit for detecting a target nucleic acid may also contain a denaturation agent for converting double stranded target nucleic acid to single stranded nucleic acid in a sample; a lysing agent for treating the sample to release nucleic acid or to allow entry of the conjugate probe; and a hybridization solution for maintaining optimal conditions to allow for specific hybridization. Optionally, the kit may also contain a solid support for immobilizing either the sample or the target nucleic acid from the sample. Alternatively, the conjugate probe can be immobilized on the support. Where it is required for detection of the labeling group, a signal molecule may also be provided. Appropriate washing buffer to maintain stringency and specificity of the binding reaction may also be provided.

A kit for making conjugate probes is also provided. The kit must contain polymerized aldehyde and a buffer solution necessary for production of conjugate probes. The polymerized aldehyde may have a molecular weight that is optimal for the conjugate probe to be made. Optionally, it may contain any or all of the elements necessary for making the conjugate probe.

The present invention will be further understood by reference to the following non-limiting examples.

EXAMPLE 1

Preparation of Polyglutaraldehyde 1. 1–5 M NaOH is added to a 5–50% (25% optimal) Glutaraldehyde solution until the pH is 8.0–11.75 (optimal pH—10.0).
2. The solution is stirred at room temperature for 2–24 hours (4 hours optimal).
3. 1–5 M HCl is then added to lower the pH to 2.0–7.0 (optimal pH—4.0).
4. Under optimal conditions, no precipitate or cloudiness should appear in the solution during the reaction (step 2) or acidification (step 3). If, however, precipitate is visible or if the solution appears cloudy, then the solution is purified by filtration. The solution is first filtered by gravity filtration through Whatman 1 (or equivalent) filter paper, followed by a vacuum filtration through a 0.2 micron filter. The solid material is discarded and the clear filtrate which contains water-soluble polyglutaraldehyde is retained.
5. The polyglutaraldehyde is stored as an aqueous solution at 4° C.

EXAMPLE 2

Spectrophotometric Characterization of Polyglutaraldehyde Solutions

Pure monomeric glutaraldehyde shows a single UV adsorption maxima at 280 nm. Polyglutaraldehyde prepared under optimal conditions shows a single UV adsorption maxima at 235 nm. A 25% glutaraldehyde solution which is converted to water soluble polyglutaraldehyde under optimal condition gives a 235 nm absorption of approximately 0.50 when diluted 1000 fold in deionized water and read in a spectrophotometer with a path length of 1 cm. Water soluble polyglutaraldehyde prepared at high pH may show an absorbance peak at 290 nm. (*J. Ultrastructure Res.* 30:275–287 (1970)).

Nucleic acid probes made from water-soluble polyglutaraldehyde prepared at a pH greater than 10 show good signal, but higher background when used in in-situ hybridization. Nucleic acid probes made from the material prepared at a pH lower than optimal give equivalent or slightly lower signal when used in in-situ hybridization.

The 235 nm absorption of a 25% polyglutaraldehyde solution is proportional to the initial pH at which it was formed. The higher the initial pH, the higher the 235 nm optical density.

EXAMPLE 3

Molecular Weight Characterization of Polyglutaraldehyde

The molecular weight of water soluble polyglutaraldehyde was characterized by gel filtration chromatography. A dilute sample of water soluble polyglutaraldehyde was applied to a SEPHADEX™ G-10 and G-25 column. The elution was followed by monitoring the optical density of the column effluent at 235 nm as it passed through a spectrophotometer flowcell. The column void volumes and elution times were determined in a similar manner with the large polymer, blue dextran, using a wavelength of 635 nm. In gel filtration chromatography, molecules larger than the MW cutoff size of the gel pass through the column in the void volume. Molecules smaller than the cutoff volume are retained in the column and are eluted by the addition of more solvent to the column, as a function of molecular weight.

Greater than 90% of the polyglutaraldehyde was retained on a G-10 column having a molecular weight cutoff of 700. 100% of the polyglutaraldehyde was retained on a G-25 column having a molecular weight cutoff of 5000.

EXAMPLE 4

β-phycoerythrin-DNA Conjugates

The ability of glutaraldehyde and polyglutaraldehyde to conjugate single stranded DNA to β-phycoerythrin was compared. The polyglutaraldehyde was able to conjugate β-phycoerythrin to DNA; however, glutaraldehyde was ineffective at conjugating β-phycoerythrin to DNA.

The following mixtures were prepared and incubated: DNA with β-phycoerythrin, β-phycoerythrin with phycoerythrin and DNA with DNA.

|  | A | B |
|---|---|---|
| β-phycoerythrin (20 μg) | 11.7 μl | 11.7 μl |
| glutaraldehyde (10%) | 2 μl (poly) | 2 μl (mono) |
| single stranded DNA (10 μg) | 6.7 μl | 6.7 μl |
| H$_2$O | 0 μl | 0 μl |

|  | C | D |
|---|---|---|
| β-phycoerythrin (20 μg) | 11.6 μl | 0 μl |
| glutaraldehyde (10%) | 2 μl (poly) | 2 μl (mono) |
| single stranded DNA (10 μg) | 0 μl | 6.7 μl |
| H$_2$O | 6.7 μl | 11.7 μl |

|  | E | F |
|---|---|---|
| β-phycoerythrin (20 μg) | 0 μl | 11.7 μl |
| glutaraldehyde (10%) | 2 μl (poly) | 2 μl (mono) |
| single stranded DNA (10 μg) | 6.7 μl | 0 μl |
| H$_2$O | 11.7 μl | 6.7 μl |

The final concentration of conjugating agent in each mixture was 1.0%. The mixtures were incubated at 37° C. for one hour and then cooled in an ice bath until analyzed by electrophoresis. Electrophoresis was carried out on eight samples in adjacent wells on an agarose gel on samples of:

(1) DNA (control)

(2) β-phycoerythrin (control)

(3) polyglutaraldehyde with DNA and β-phycoerythrin (4) polyglutaraldehyde with DNA, without phycoerythrin (5) polyglutaraldehyde with β-phycoerythrin, without DNA (6) glutaraldehyde with DNA and β-phycoerythrin (7) glutaraldehyde with DNA without phycoerythrin (8) glutaraldehyde with β-phycoerythrin without DNA β-phycoerythrin fluoresces red and can be easily seen without staining. Samples 1 and 2 are standard controls which indicate the migration patterns of DNA and β-phycoerythrin, respectively, under the influence of an electric current in an agarose gel. Samples 3, 4, and 5 contain polyglutaraldehyde. Same 3 shows a delayed migration pattern relative to β-phycoerythrin and thus indicates the presence of both β-phycoerythrin and of DNA. In order to confirm this, the electrophoresis gel was then stained with toluidine blue to show the presence of DNA, confirming the sample contains both β-phycoerythrin and DNA. This indicates that conjugation occurred between DNA and β-phycoerythrin in the presence of polyglutaraldehyde.

Sample 4 shows that polyglutaraldehyde is unreactive in crosslinking DNA with DNA. However, Sample 5 illustrates the effectiveness of polyglutaraldehyde in crosslinking proteins to proteins, since no DNA is present but the migration of the BPE into the gel is prevented.

Sample 6, 7, and 8 contain glutaraldehyde. Samples 6 and 8 show a migration pattern typical of β-phycoerythrin. Sample 7 shows a pattern identical to Sample 1. Taken together, Samples 6, 7, and 8 indicate that conjugation in the presence of glutaraldehyde did not occur.

EXAMPLE 5

Horseradish Peroxidase-DNA Conjugates

The ability of polyglutaraldehyde and glutaraldehyde to conjugate single stranded DNA to horseradish peroxidase was evaluated. The results show that polyglutaraldehyde can conjugate large amounts of horseradish peroxidase to DNA.

The following mixtures were prepared in ratios of labeling group to DNA of 1:1, 2:1, 4:1 and 8:1, respectively.

| | |
|---|---|
| 1:1: | 1 μl 10 mg/ml/horseradish peroxidase |
| | 2.5 μl polyglutaraldehyde (10%) |
| | 4.16 μl single stranded DNA (2.4 mg/ml) |
| | 2.34 μl H$_2$O |
| 2:1 | 1 μl 20 mg/ml horseradish peroxidase |
| | 2.5 μl polyglutaraldehyde (10%) |
| | 4.1 μl single stranded DNA (2.4 mg/ml) |
| | 2.34 μl H$_2$O |
| 4:1: | 2 μl 20 mg/ml horseradish peroxidase |
| | 2.5 μl polyglutaraldehyde (10%) |
| | 4.1 μl single stranded DNA (2.4 mg/ml) |
| | 1.34 μl H$_2$O |
| 8:1: | 4 μl 20 mg/ml horseradish peroxidase |
| | 2.5 μl polyglutaraldehyde (10%) |
| | 4.16 μl single stranded DNA (2.4 mg/ml) |
| | 0 μl H$_2$O |

The mixtures were incubated at 37° C. for 45 minutes and then cooled in an ice bath until analyzed by electrophoresis. The final concentration of conjugating agent in each mixture was 2.5%.

Electrophoresis was carried out on the samples in adjacent wells on an agarose gel. From left to right the samples were as follows. They contain horseradish peroxidase to DNA ratios of 1:1, 2:1, 4:1 and 8:1, respectively.

The electrophoresis gel was stained with nickel enhanced diaminobenzidine/H$_2$O$_2$. Horseradish peroxidase is detected by deposition of a black precipitate. DNA is below detectable levels.

The presence of horseradish peroxidase is indicated by the blackened portions of the gel. The presence of higher molecular weight conjugates is indicated by slow migration relative to lower molecular weight conjugates. In samples 1, 2, 3, and 4, the pattern of migration indicates that the molecular weight of the conjugate increased as the ratio of horseradish peroxidase to DNA increased. In each successive sample, the pattern of migration is shorter.

EXAMPLE 6

Signal Analysis of Probes

For conjugate probes that hybridize in situ, it is ideal to obtain a strong, easily detectable signal and no background noise that might obscure the signal. The greater the quantity of detectable protein in the probe, the stronger the signal. Polyglutaraldehyde conjugate probes having a horseradish peroxidase to DNA ratio of 4:1 gave the highest detectable signal. The probes having an 8:1 ratio gave an equivalent signal to those having a 4:1 ratio. When the signal and background noise of conjugate probes having a 4:1 ratio were measured at 2.5 μg/ml. 2.5 μg/ml was found to give the highest signal without measurable background noise.

Conjugate probes composed of horseradish peroxidase, DNA and 2.5% polyglutaraldehyde were prepared as described in Example 2 and hybridized to test cells in situ. Samples having horseradish peroxidase to DNA ratios of 1:2, 1:1, 2:1, 4:1, and 8:1 were prepared. Eukaryotic target cells for which the probe DNA was specific were fixed to glass slides by a standard ethanol procedure. Signal and background noise were measured by microscopic observation.

When the signal from conjugate probes having different horseradish peroxidase to DNA mass ratios were compared, the signal increased from 1:2 to 4:1 and leveled off. The amount of signal at 4:1 and at 8:1 was equivalent. Background noise was measured through the same range of mass ratios. Background noise was effectively zero between 1:2 and 4:1, but increased above zero between 4:1 and 8:1.

EXAMPLE 7

Specificity Analysis of Conjugate Probes Made with Polyglutaraldehyde

It is well known that covalent bonding between molecules alters their local properties. The specificity of nucleic acid probes depends upon the attraction between the nucleic acid moiety and its target nucleic acid. The specificity of polyglutaraldehyde conjugated probes was tested by hybridizing the probes to the DNA of cells known to contain DNA complementary to the probe nucleic acids.

The probe DNA was shown to have specificity by hybridizing with its intended target in every instance and failing to hybridize with non-target DNA in every instance. Therefore, polyglutaraldehyde does not reduce the specificity of conjugate probes for their targets.

Conjugate probes were prepared by sonicating plasmids containing DNA of a specific virus. The probes were prepared and incubated to make conjugate probes having a labeling group to DNA ratio of 4:1 as described above. Target cells were fixed on microscope slides by an alcohol procedure. Conjugate probes having a solution concentration of 25 μg/ml were applied to target cells.

Probes containing Human Papilloma virus #16 (HPV16), Human Papilloma virus #11 (HPV11), Cytomegalo virus (PRA4), Herpes virus (4L) and Human specific sequence (PHC), respectively, were reacted with Caski and LTK-gpt cells and with cytomegalovirus (CMW) and herpes simplex virus (HSV) containing cells.

Caski cells are a transformed human cell line that contains integrated HPV16 sequence. A probe containing either HPV16 DNA or PHC DNA would be expected to hybridize with DNA in the Caski cell. LTK-gpt cells contain DNA present in each probe plasmid, so they should react with all probes.

Each of the conjugate probes tested would be expected to hybridize to its respective homologous DNA target.

DNA probes labeled with horseradish peroxidase gave significant signals in an HPV test in Caski cells only when the glutaraldehyde solutions utilized in the preparation of the DNA probe contain significant amounts of polyglutaraldehyde. When a commercial glutaraldehyde solution was utilized (Fluka), no significant signal was detected. Results were essentially the same using LTK cells in the test.

If the extent of signal in hybridization is correlated against the extent of glutaraldehyde polymerization in aqueous glutaraldehyde solutions, it is evident that the higher the amount of polyglutaraldehyde in glutaraldehyde solutions, the higher the signal. The Caski cells showed higher signals than the LTK cells.

These experiments confirm that the normally available commercial solutions of glutaraldehyde do not contain any significant amount of polymerized glutaraldehyde. Furthermore, without significant amounts of polymerized glutaraldehyde, the commercial solutions of glutaraldehyde do not yield conjugate probes which can be successfully utilized in hybridization experiments.

EXAMPLE 8
The Analysis of Glucose Oxidase-DNA Conjugates by Sandwich Hybridization The presence of glucose oxidase-DNA conjugate probes made with polyglutaraldehyde was determined by sandwich hybridization. The system of sandwich hybridization used consists of hybridizing a chemically biotinylated DNA probe to a complementary glucose oxidase-DNA probe synthesized using polyglutaraldehyde. The hybrids were isolated by reacting the hybridization mixture with avidin that had been immobilized on a microtiter well. After washing, only the unreacted biotinylated DNA and biotinylated DNA hybridized to the complementary glucose oxidase DNA remained in the well. The well was then reacted with a signal reagent that turns blue in the presence of glucose oxidase but is unaffected by biotin labeled DNA. Hence, a blue color would indicate that glucose oxidase was bound to a DNA which hybridized to a DNA containing biotin. If glucose oxidase was not bound to the DNA probe or if that probe could not hybridize to the biotinylated target, no enzyme and (thus no color) would remain in the well following washing.

A conjugation mixture was prepared by adding:

22 µl single-stranded DNA (20 µg);
1.0 µl glucose oxidase (40 µg);
3.0 µl 10% polyglutaraldehyde: 4.0 µl $H_2O$.

This mixture was incubated at 37° C. for one hour and kept on ice.

Hybridization was performed using: 1.0 µl of glucose oxidase-DNA conjugate probe (667 ng) hybridized to 460 ng of single-stranded biotinylated DNA in 1.2×SSC (0.2 M $Na^+$); 0.6 mg/ml yeast RNA, 5.0% polyethylene glycol in 50 µl total volume at 50° C. for one hour, allowed to cool to room temperature, then placed on ice.

Microtiter wells were coated with avidin and a collection of hybrids using 50 µl of 0.1 mg/ml avidin in 50 mM sodium bicarbonate placed on the bottom of each well of a 96-well microtiter plate and allowed to sit undisturbed at room temperature for 90 minutes. The avidin was removed, and each well was rinsed 10 times with 1× phosphate buffered saline (PBS, 8 MM $PO_4$, pH 7.2, 15 mM NaCl) and blocked with 100 µl of 3% Bovine Serum Albumin (BSA) 0.4 M NaCl 0.1 M sodium bicarbonate. After 60 minutes of blocking, 65 µl of the BSA solution was removed and 5 µl of hybridization mix was added. At room temperature, the plate was shaken for 30 minutes, rinsed 10 times with a 0.6× solution of sodium saline citrate (SSC 90 mM NaCl and 9.0 mM sodium citrate) pH 7.2 washed 3 times for 10 minutes, each time with 0.6×SSC, 0.2% sodium dodecyl sulfate (SDS), and re-rinsed 10 times with 0.6×SSC.

Colorometric determination of the extent of hybridization was made by reacting each well for 3.5 minutes with 200 µl of glucose oxidase reagent containing 0.6 µg/ml horseradish peroxidase, 10% B-D glucose, 0.1 mg/ml tetramethylbenzidine in dimethyl sulfoxide (DMSO), 50 mM NaAc pH 5.0. The reaction was stopped with 100 µl 2.0 M $H_2SO_4$, and the optical density (OD) at 450 nm was recorded spectrophotometrically The results were as follows with DNA-glucose oxidase as the probe, and complementary biotinylated DNA as the target: $OD_{450}$ 0.669; With DNA-glucose oxidase as the probe and non-complementary biotinylated DNA as the target: $OD_{450}$ 0.106. The results demonstrate that significant color was seen only when a conjugate probe complementary to a biotin labeled target was present.

EXAMPLE 9
Analysis of Alkaline Phosphatase-DNA Conjugates by Sandwich Hybridization The presence of alkaline phosphatase-DNA conjugates made with polyglutaraldehyde was determined by sandwich hybridization of two non-homologous probes to target DNA.

The system of sandwich hybridization used involved hybridizing a chemically biotinylated DNA conjugate probe and an alkaline phosphatase DNA probe to target DNA that will hybridize to both probes such that after hybridization the two probes will be linked via the target. The two probes used in this system have little or no homology to each other. The hybrids were isolated by avidin-biotin binding as described in the previous example and were reacted overnight with alkaline phosphatase reagent (15 mM p-nitrophenylphosphate). The presence of yellow color indicated the presence of the hybrid described above.

The amount of hybridized alkaline phosphatase-DNA probe in each sample was indicated by the optical density of yellow color. A background color density was measured in a control sample containing no target DNA. A conjugation mixture was prepared by adding:

6.7 µl single-stranded DNA (10 µg);
10.0 µl alkaline phosphatase (20 µg);
5.0 µl 1.0% polyglutaraldehyde; and
28.3 µl $H_2O$.

This mixture was incubated at 37° C. for 30 minutes, then placed on ice.

Hybridizations were carried out using 200 pg/µl alkaline phosphatase-DNA conjugate probe, 200 pg/µl biotinylated-DNA probe, 1.2×SSC (0.2 M Na+), 0.1% SDS, 0.6 mg/ml yeast RNA, 5.0% polyethylene glycol, 17 mM Tris pH 8.8, 1.7 mM $MgCl_2$, 4.15 mM $(NH_4)_2SO_4$, 1.7µM ethylene diamine tetraacetic acid (EDTA), 0.25% DMSO. Various concentrations of target DNA were hybridized in the above solution for two hours at 50° C. in 50 µl total volume.

250 µl of 0.1 mg/ml avidin was placed in each well of a 24-well microtiter dish and allowed to set undisturbed at room temperature for 2.5 hours. The avidin was removed, and each well was rinsed 10 times with 1.0×PBS and blocked for one hour with 5 µl of 3.0% BSA 0.4 M NaCl 0.1 M sodium bicarbonate. After blocking, 300 µl of the BSA solution was removed, and the entire 50 µl of hybridization mix was added to the well. The plate was reacted and washed as described in Example 5.

Each well was reacted with 300 µl of 15 mM p-nitrophenylphosphate in 0.1 M diethanolamine, 1.0 MM MgCl$_2$ pH 9.8 overnight at room temperature. The absorbance at 405 nm of the solutions were recorded spectrophotometrically.

| Results | | |
|---|---|---|
| Character of Target | Amount of Target | OD$_{405}$ |
| Hybridizable | 70 pg | 0.489 |
|  | 20 pg | 0.218 |
|  | 10 pg | 0.142 |
| Control | — | 0.098 |

EXAMPLE 10
Conjugation of Urokinase, Apoaquorin, and Alcohol Oxidase to PolyA Using Polyglutaraldehyde Polyribonucleic acid (PolyA) was used to demonstrate that conjugates of nucleic acid and virtually any protein can be formed using polyglutaraldehyde. Affinity chromatography on oligo-dT-cellulose readily separates unconjugated protein from polyA-protein conjugates.

The results show that polyglutaraldehyde will conjugate randomly chosen proteins to nucleic acid.

The "conjugation mixture" is poly-A, protein, and polyglutaraldehyde. The "mixture" is poly-A and protein with no polyglutaraldehyde. The "mock conjugation mixture" is protein and poly-glutaraldehyde with no poly-A.

Conjugation mixtures were prepared as follows:

| | |
|---|---|
| A: 35 µl urokinase (17 µg) | B: 3.16 µl apoaquorin (50 µg) |
|   5 µl 1% polyglutaraldehyde |   5 µl 10% polyglutaraldehyde |
|  10 µl RNA (25 µg) |  10 µl RNA (25 µg) |
|   0 µl H$_2$O |  31.4 µl H$_2$O |
| C: 1 µl alcohol oxidase (50 µg) | |
|   5 µl 1% polyglutaraldehyde | |
|  10 µl RNA (25 µg) | |
|  34 µl H$_2$O | |

Each mixture was incubated for one hour at 37° C., then analyzed by Oligo-dT cellulose chromatography. About 0.1 g of oligo-dT cellulose (Collaborative Research) was equilibrated to 20 mM sodium citrate, 0.4 M NaCl, pH 7.2. The conjugate mix was adjusted to the same salt concentration, applied to the top of the column and allowed to adsorb onto the resin. The column was then washed with about 10 ml of the above buffer, saving the first two 1.5 ml fractions. These wash fractions contained unconjugated protein and excess polyglutaraldehyde. The column was then eluted with 10 ml of distilled water, again saving the first two 1.5 ml fractions. These elution fractions contained unconjugated polyA and polyA-protein conjugate.

The amount of protein was measured using the absorbance at 260 nm and the Biorad Protein Assay. 400 µl of each saved fraction was reacted with 100 µl Biorad Protein Assay solution for 10 minutes, and the OD at 595 nm was recorded spectrophotometrically.

$$\% \text{ protein conjugated} = \frac{OD_{595} \text{ fraction \#1}}{OD_{595} \text{ elution fraction \#1} + OD_{595} \text{ wash fraction \#1}}$$

| Sample | % Protein Conjugated |
|---|---|
| polyA apoaquorin conjugate | 99% |
| polyA apoaquorin mixture | 0% |
| polyA apoaquorin mock conjugate | 0% |
| polyA urokinase conjugate | 83% |
| polyA urokinase mixture | 0% |
| polyA urokinase mock conjugate | 0% |
| polyA alcohol Oxidase conjugate | 32% |
| polyA alcohol Oxidase mixture | 0% |
| polyA alcohol Oxidase mock conjugate | 0% |

Even though the percentage of protein conjugated varies, each protein is conjugated with polyglutaraldehyde. The conjugation procedure for each individual protein can be optimized to yield higher amounts of protein bound in the conjugate.

EXAMPLE 11
Conjugation of Avidin Horseradish Peroxidase

The wells of a 96-well microtiter plate were coated with a 50 µl solution of avidin at a concentration of 0.1 mg/ml in a solution of 50 mM sodium bicarbonate (BSA) pH 8.1 for one hour. The solution was removed from the wells. The wells were rinsed ten times with 1×(PBS), and blocked with 200 ml of blocking solution (3% BSA, 0.4 M NaCl, 0.1 M sodium bicarbonate) for 30 minutes.

145 µl of blocking solution was removed from one-half of the wells and 5.0 µl of a solution of single-stranded biotinylated DNA at a concentration of 400 pg/µl was added. The plate was shaken for 30 minutes, washed ten times with 1×PBS, and re-blocked with 200 ml of blocking solution for 30 minutes.

145 µl of blocking solution was removed from all of the wells and 5.0 µl of avidin-horseradish peroxidase suspected conjugate in blocking solution at concentrations of 100 ng/µl, 20 ng/µl, 4 mg/µl, and 0.8 ng/µl was added to selected wells. The wells were shaken for 30 minutes and then washed ten times with 1×PBS solution. Each well was reacted with 200 µl tetramethylbenzidine (TMB) for 20 minutes. The reaction was stopped with 2.0 M H$_2$SO$_4$. An optical density reading at 450 nm was recorded. The results are as follows:

A. Avidin Wells Reacted with 2 ng Single-Stranded Biotinylated DNA OD450 for Amount of Avidin + Horseradish Peroxidase Applied to Each Well

| 500 ng | 100 ng | 20 ng | 4 ng | 0.8 ng |
|---|---|---|---|---|
| Conjugate: Avidin + Horseradish Peroxidase + Polyglutaraldehyde | | | | |
| 0.175 | 0.125 | 0.084 | 0.037 | 0.033 |
| Conjugate: Avidin + Horseradish Peroxidase + no Polyglutaraldehyde | | | | |
| 0.019 | 0.020 | 0.023 | 0.024 | 0.023 |

| B. Avidin Wells Not Reacted with Biotinylated DNA $OD_{450}$ for Amount of Avidin + Horseradish Peroxidase Applied to Each Well | | | | |
|---|---|---|---|---|
| 500 ng | 100 ng | 20 ng | 4 ng | 0.8 ng |
| Conjugate: Avidin + Horseradish Peroxidase + Polyglutaraldehyde | | | | |
| 0.026 | 0.029 | 0.018 | 0.015 | 0.032 |
| Conjugate: Avidin + Horseradish Peroxidase + no Polyglutaraldehyde | | | | |
| 0.018 | 0.022 | 0.023 | 0.034 | 0.055 |

The results show that conjugation of horseradish peroxidase to avidin occurs only in the presence of polyglutaraldehyde (Results A), and that neither avidin plus horseradish peroxidase conjugate or mixture bind nonspecifically to an avidin-coated well. Twenty ng of avidin plus horseradish peroxidase conjugate can be detected by this method.

EXAMPLE 12
Determination of Minimum Concentration for Mating Conjugate Probe Conjugate probes were made using DNA from human specific sequence (PHC) and cytomegalovirus (PRA4) with horseradish peroxidase at a mass ratio of 4:1 of enzyme to DNA. The conjugation mixture contained 2.5% polyglutaraldehyde. The mixture was incubated for 45 minutes at 37° C. in buffer solution at pH 6.5–7.0. Each conjugate probe was mixed to final reagent concentrations of 1.0 mg/ml, 0.5 mg/ml, 0.25 mg/ml and 0.10 mg/ml before dilution. The quality of conjugates made at these concentrations was compared by measuring the signal from hybrids formed from these conjugates with target DNA.

Each conjugate probe solution was diluted in hybridization buffer to 10 µg/ml to make a hybridization mixture. Hybridization solution (25 µl) was applied to microscope slides with wells containing LTK-gpt and CMV target cells. Hybridization took place for 20–60 minutes at 37° C. in a humid chamber. The wells were washed for 10 minutes, stained with DAB for 15 minutes, and counterstained with nuclear fast red.

Hybrids from conjugate probes made at 1.0 mg/ml, 0.5 mg/ml and 0.25 mg/ml produced excellent signal intensity. The signal intensity from conjugate probe made at 0.1 mg/ml was greatly diminished. The results show a non-linear relationship between the signal intensity and the change in concentration of conjugation reagents in the incubation solution between 1.0 mg/ml and 0.1 mg/ml. For each type of conjugate probe a dramatic drop in signal intensity occurs between 0.25 mg/ml and 0.1 mg/ml.

The signal intensity of a conjugate probe is affected by the reagent concentration at the time the conjugate probe is made. Effective conjugation occurs at reagent concentrations above 0.1 mg/ml.

EXAMPLE 13
Preparation and Comparison of Polyglutaraldehyde Protein Conjugates To demonstrate the ability of polyglutaraldehyde to form conjugates between proteins, a variety of protein pairs were incubated with polyglutaraldehyde and the results determined by electrophoretic analysis on an agarose gel. The proteins examined were horseradish peroxidase, glucose oxidase, alkaline phosphatase, and β-phycoerythrin.

All conjugates were prepared in a concentration of 1 mg/ml of reagent. All solutions were incubated for 60 minutes at 37° C. Samples were prepared with and without polyglutaraldehyde. Incubated samples were subjected to electrophoretic analysis on an agarose gel. The resulting migration patterns of the protein pairs were compared.

Horseradish peroxidase is a positively charged protein. Glucose oxidase, alkaline phosphatase, and β-phycoerythrin are negatively charged proteins. Conjugates can be distinguished from the unconjugated enzyme based on differences in electrophoretic mobility.

Migration patterns showed that each sample incubated with polyglutaraldehyde formed conjugates. However, samples incubated in the absence of polyglutaraldehyde exhibited the migration patterns of the unconjugated horseradish peroxidase.

EXAMPLE 14
Preparation of Polymerized Aldehyde IX

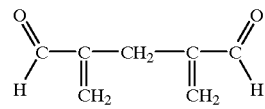

10 ml of 37% formaldehyde was mixed with 10 ml of 10% NaOH in ethanol. This mixture was stirred on a stir plate. Into the stirring alkaline formaldehyde was added 10 ml of 25% glutaraldehyde dropwise, approximately one drop per minute. After the addition of glutaraldehyde was complete, the mixture was allowed to stir for 16 hours. The solution was then neutralized to pH 7.0 with concentrated HCl. A portion of the mixture was then distilled. A UV spectrum of the fraction which distilled between 65 and 82° C. showed a single peak at 218 nm. The absorption maximum predicted by the Woodward-Feiser Rules for this polymerized aldehyde is 220 nm.

EXAMPLE 15
Preparation of Polymerized Aldehyde (X)

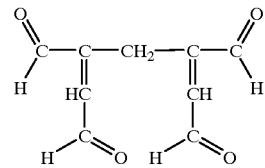

10 ml of 40% glyoxal (1,2-ethanedial) was mixed with 10 ml of 1 M NaOH. This mixture was stirred on a stir plate. 10 ml of 25% glutaraldehyde was added to this mixture dropwise, at approximately 1 drop per minute. Following the addition of the glutaraldehyde, the solution was acidified to pH 7.0 with concentrated HCl. A UV spectrum of the acidified solution showed strong absorption peaks at 230.5 nm, 292 nM, and 336 nm. The product was used without further purification.

EXAMPLE 16
Preparation of Polymerized Aldehyde (XI)

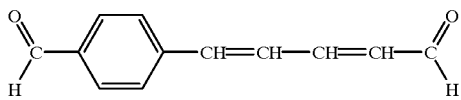

10 ml of terephthaldicarboxaldehyde is mixed with 10 ml of 1 M NaOH. The mixture is stirred on a stir plate. To this solution is added 5 ml of crotonaldehyde dropwise at a rate of one drop per minute. After the completion of the crotonaldehyde addition, the mixture is acidified with concentrated HCl to pH 7. The mixture is used without further purification.

EXAMPLE 17
Horseradish Peroxidase-DNA Conjugates Prepared with α,β-Unsaturated Aldehydes HRP-DNA conjugates were prepared in an identical manner to the 8:1 HRP-DNA conjugates prepared with polyglutaraldehyde in Example 5. The following conjugating agents were used at the concentrations listed below:

| Conjugating Agent | Concentration |
| --- | --- |
| Glutaraldehyde | 25% |
| Polyglutaraldehyde | 25% |
| Polyadipaldehyde | 10% |
| Compound IX | 1 M/l |
| Compound X | 1 M/l |

In situ hybridizations of HPV16 probes prepared with the above conjugating agents with CaSki and LTK cells were compared. In both cases, hybridizations carried out according to the procedure of example 7 with probes prepared with α,β-unsaturated aldehydes gave significant signal while the hybridization with a probe made with glutaraldehyde, a saturated aldehyde, gave no significant signal.

EXAMPLE 18
Comparative Example

Two commercially available kits that utilize in situ hybridization for the rapid detection of human papillomavirus (HPV) DNA in histological sections were compared. One kit uses biotinylated DNA probes that, after hybridization with viral DNA, are bound to a streptavidin-alkaline phosphatase conjugate. The other kit uses a new type of DNA probe, wherein the tracer enzyme horseradish peroxidase (HRP) is supplied directly attached to the nucleic acid through the water-soluble conjugating agent polyglutaraldehyde, yielding a directly labeled, water-soluble DNA probe. In the presence of particular substrates, the enzymes in each kit produce a dark precipitate at the location of probe-viral DNA hybrid formation, thereby indicating the presence of viral sequences. The biotin probe kit uses alkaline phosphatase to form a nuclear and sometimes cytoplasmic blue-purple precipitate. The direct-label kit uses HRP to form a heavy metal-modified diaminobenzidine (DAB) precipitate which is enhanced by a 2-step silver technique to result in a very highly localized nuclear jet-black precipitate that generally has greater signal intensity and hence is easer to interpret.

The direct-label system was much more type-specific than its biotin counterpart. Extensive cross-hybridization of probe with target prevented the biotinylated DNA probe system from making an unambiguous identification in most cases, while a particular HPV type could be clearly identified by the highly specific direct-label system. High stringency hybridizations confirmed the accuracy of the direct-label probes.

EXAMPLE 19
Use of Polymerized Aldehyde IX to Bind Macromolecules to Solid Supports Polymerized aldehyde IX, preferably prepared as described in Example 14, is diluted to 0.1 M/l in phosphate buffered saline (PBS). 200 μl of solution is added to each well of a polystyrene microtiter plate. After a ten minute incubation, the solution is removed and the wells are rinsed with 10 changes of PBS. A solution of avidin, 0.1 mg/ml in pH 9.0 carbonate buffer, is added to each well. The avidin solution is incubated in the wells for 30 minutes. The wells are then rinsed with ten changes of PBS. 12.5 ng pRA4 DNA or sheared herring sperm (SHS) DNA is then bound to the avidin coated well using the following steps:

1. The DNA is diluted to a 10× concentration (125 ng in 100 μl) in 1× PBS.
2. The DNA in 1× PBS is denatured by heating for 3 minutes at 95° C.
3. The DNA is diluted to 1× concentration (12.5 ng in 100 μl) with 4 M ammonium acetate, pH 4.0.
4. 100 μl (12.5 ng) of the DNA solution is added to a microtiter plate well.
5. The DNA solution is incubated in the microtiter plate well for one hour at room temperature.
6. The microtiter plate well is washed ten times with 1× PBS.

After washing, the bound DNA is detected by subsequent hybridization with a pRA4-complementary HRP-labeled DNA probe. The wells are washed again, and a color development solution of tetramethylbenzidene (TMB) and hydrogen peroxide in 50 mM Acetate buffer, pH 4.0, is added to the wells. The generation of color indicates the presence of bound HRP-DNA and thus the presence of avidin (necessary for binding the DNA).

The results were as follows:

|  | Signal | Background* | S/N |
| --- | --- | --- | --- |
| $OD_{450}$ using Compound IX | 1.731 | 0.182 | 4.5 |
| $OD_{450}$ without using Compound IX | 1.059 | 0.932 | 1.1 |

*Background is signal generated from the non-specific binding of pRA4-complementary probe to bound sheared herring sperm DNA.

EXAMPLE 20
Direct Conjugation of AMCA to DNA Through Polyglutaraldebyde 7-amino-4-methylcoumarin hydrazide (AMCA-hydrazide) was conjugated to DNA through polyglutaraldehyde (PGA).

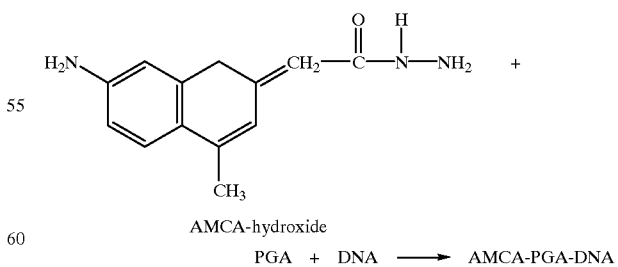

AMCA-hydroxide

PGA + DNA ⟶ AMCA-PGA-DNA

Preparation

I. Sonicated HVP11 DNA (cloned into pUC) was denatured at 100° C. for 3 minutes. The ingredients were then mixed together in the following order:

```
12.2 µl DNA (100 µg)
10.0 µl 25% Polyglutaraldehyde prepared at pH 10.0
67.8 µl Labelling Buffer - 10 mM Acetate, pH 4.75

90.0 µl
```

The above solution was incubated for one hour at 37° C. At the same time, a stock solution of saturated AMCA-hydrazide was prepared by adding 1 mg AMCA-hydrazide to 100 µl dry dimethylformamide (DMF). The solution was vortexed until no more solid would dissolve. The undissolved solid was allowed to settle to the bottom.

When the 37° C. incubation was complete, 10 µl of AMCA-hydrazide stock solution was added to the reaction mixture. The labelling reaction was allowed to proceed for one hour at room temperature.

II. The process was repeated except that the labelling buffer was 100 mM sodium acetate, pH 5.0.

III. HPV11 DNA was denatured for 3 minutes at 100° C. The following ingredients were then added in the following order:

```
24.4 µl DNA (200 µg)
20.0 µl 25% Polyglutaraldehyde prepared at pH 10.0
55.6 µl deionized water 100 µl
```

The above solution was incubated for one hour at 37° C.

A G-25 spin column was prepared by packing a 0.7×4 cm column with Sephadex G-25. The column was equilibrated with 10 mM acetate, pH 4.75. Excess liquid was removed from the column by centrifugation at 1600 g for twelve minutes.

Following incubation, the reaction mixture was applied to the spin column. The column was centrifuged at 1600 g for twelve minutes and the column eluent was collected. The eluent contains 'activated' DNA, i.e., the purified reaction product of the polyglutaraldehyde and DNA.

The 'activated' DNA was labelled with AMCA hydrazide by combining in the following order:

```
50 µl activated DNA (100 µg DNA)
40 µl Labelling buffer - 10 mM acetate, pH 4.75
10 µl AMCA-hydrazide stock solution in DMF 100 µl
```

The above mixture was incubated for one hour at 37° C.

IV. The process of III was repeated except that the labelling buffer was 100 mM sodium acetate, pH 5.0.

All of the conjugates (DNA-PGA-AMCA) were purified in an identical manner. A 1×8 cm chromatography column was gravity packed with SEPHADEX™ G-50. The column was equilibrated with 1×PBS and the solvent was drained to the top of the column bed. The reaction mixture (100 µl) was added to the top of the column bed. After letting the conjugate drain into the column, additional solvent was added to the top of the column bed. The migration of the conjugate and free AMCA-hydrazide was monitored by illuminating the column with a long wave (366 nm) UV lamp.

On the column, the reaction mixture separated into two separate bands of approximately equal intensity but slightly different color. One band moved very slowly through the column while the other migrated very rapidly through the column. The rapidly moving band was eluted from the column and was collected in a total volume of approximately 1.5 ml. The slow-moving fluorescent band could only be eluted from the column after repeated washings with 1×PBS.

The purified conjugates (DNA-PGA-AMCA) were characterized spectroscopically. The results are summarized in the table below.

| Conjugate | [1]$OD_{345-390}$ | $OD_{260}$ | [DNA] µg/ml | [AMCA] M/L | [2][Bases] [AMCA] |
|---|---|---|---|---|---|
| AMCA-hydrazide (unconjugated) | .587 | .094 | 0.00 | 3.28e-5 | — |
| I | .631 | .832 | 58.5 | 7.05e-5 | 2.5 |
| II | .425 | .708 | 51.2 | 4.75e-5 | 3.3 |
| III | .495 | .900 | 65.7 | 5.53e-5 | 3.6 |
| IV | .655 | 1.099 | 79.5 | 7.32e-5 | 3.3 |

[1]The absorption maximum of the AMCA label shifts slightly upon conjugation to DNA.
[2]The average number of bases per fluorescent label.

The observation that the reaction mixture separates into two separate fluorescent bands when chromatographed on a Sephadex G-50 column indicates the presence of two populations of fluorescent material. The fluorescent band which moved very rapidly through the column must be of high molecular weight since low molecular weight species are retained by a G-50 column. A spectrophotometric analysis of the high molecular weight fluorescent fraction shows that it contains both fluorescent label (a high $OD_{380}$) and DNA (a high $OD_{260}$). Unconjugated AMCA-hydrazide shows only minimal absorbance at 260 nm. Thus, the fluorescent high molecular weight fraction purified from the reaction mixture is a conjugate consisting of DNA, polyglutaraldehyde, and AMCA-hydrazide. An unpredicted result off these experiments was the very high AMCA to DNA ratio in the conjugates that were prepared.

While the invention has been described in connection with specific embodiments thereof, it will be understood that it is capable of further modifications. This application is intended to cover any variations, uses or adaptations of the invention following, in general, the principles of the invention and including such departures from the present disclosures as come within known and customary practice within the art to which the invention pertains.

We claim:

1. A labeled conjugate probe comprising:
   a labeling group conjugated to
   a water-soluble polyglutaraldehyde prepared by polymerization at a pH of between 8 and 12 for up to about 48 hours, then acidifying to a pH of between 2 and 7, then separating the water-soluble polyglutaraldehyde from any water-insoluble polyglutaraldehyde,
   wherein the water-soluble polyglutaraldehyde is bound to a probe molecule selected from the group consisting of proteins, nucleic acids, carbohydrates, and lipids.

2. The conjugate probe of claim 1 wherein the proteins are selected from the group consisting of antigens, antibodies, receptors, and ligands.

3. The conjugate probe of claim 1 wherein the nucleic acid is selected from the group consisting of single and double stranded DNA and RNA.

4. The conjugate probe of claim 3 having a labeling group to nucleic acid mass ratio from 1:2 to 15:1.

5. The conjugate probe of claim 4 wherein the ratio is from 2:1 to 10:1.

6. The conjugate probe of claim 5 wherein the ratio is from 4:1 to 8:1.

7. The conjugate probe of claim 1 wherein the labeling group is selected from the group consisting of antibodies, zymogen activators, antigens, colored or fluorescent dyes, enzymes, chemiluminescent labels, phycobilins, ferritin, nucleic acid binding proteins, and radiolabels.

8. The conjugate probe of claim 1 wherein the probe specifically binds to a target molecule is selected from the group consisting of antigens, antibodies, receptor molecules, receptor ligands, single and double stranded DNA and RNA.

9. The conjugate probe of claim 8 wherein the target molecule is single or double stranded viral DNA or RNA.

10. The conjugate probe of claim 1 bound to a solid support.

11. A conjugate probe comprising
a labeling group conjugate to
a water-soluble polymeric unsaturated aldehyde selected from the group consisting of alpha-beta unsaturated aldehydes other than polyglutaraldehyde, aryl aldehydes, and aldehydes containing both alpha-beta unsaturated and aryl aldehyde groups, and unsaturated aldehydes thereof containing additional unsaturation,
wherein the aldehyde is bound to a probe molecule selected from the group consisting of proteins, nucleic acids, carbohydrates, and lipids.

12. The conjugate probe of claim 11 wherein the alpha-beta unsaturated aldehyde is selected from the group consisting of polyadipaldehyde, 2,4-biformyl-1,5-pentadiene, and 3,5-biformyl-2,6-heptadiene-1,7-dial and wherein the aldehyde containing both alpha-beta unsaturated and aryl unsaturated groups is 4-(1,5-pentadiene-5-al) benzaldehyde.

13. The conjugate probe of claim 11 bound to a solid support.

14. A method of preparing a labelled conjugate probe comprising
attaching a water-soluble polyglutaraldehyde prepared by polymerization at a pH of between 8 and 12 for up to about 48 hours, then acidifying to a pH of between 2 and 7, then separating the water-soluble polyglutaraldehyde from any water-insoluble polyglutaraldehyde, to
a labeling group and
a probe molecule selected from the group consisting of proteins, nucleic acids, carbohydrate, and lipid.

15. The method of claim 14 wherein the labeling group is selected from the group consisting of antibodies, zymogen activators, antigens, colored or fluorescent dyes, enzymes, chemiluminescent labels, phycobilins, ferritin, nucleic acid binding proteins, and radiolabels.

16. The method of claim 14 wherein the proteins are selected from the group consisting of antigens, antibodies, receptors, and ligands.

17. The method of claim 14 wherein the nucleic acid is selected from the group consisting of single and double stranded DNA and RNA.

18. A method of preparing a labelled conjugate probe comprising attaching a water-soluble polymeric unsaturated aldehyde selected from the group consisting of alpha-beta unsaturated aldehydes other than polyglutaraldehyde, aryl aldehydes, and aldehydes containing both alpha-beta unsaturated and aryl aldehyde groups, and unsaturated aldehydes thereof containing additional unsaturation, to
a labeling group and
a probe molecule selected from the group consisting of proteins, nucleic acids, carbohydrate, and lipid.

19. The method of claim 18 wherein the alpha beta unsaturated aldehyde is selected from the group consisting of volvadivaldehyde, 2,4-biformyl-1,5-pentadiene, and 3,5-biformyl-2,6-heptadiene-1,7-dial and wherein the aldehyde containing both alpha-beta unsaturated and aryl unsaturated groups is 4-(1,5-pentadiene-5-al) benzaldehyde.

20. A method of detecting a target molecule in a biological sample comprising the steps of:
a) reacting a labeled conjugate probe with the sample;
b) binding the labeled conjugate to the target molecule in the sample to form a complex; and
c) detecting the label of the bound conjugate, wherein detection of the label indicates the presence of the target molecule,
wherein the target molecule is selected from the group consisting of antigens, antibodies, receptor molecules, receptor ligands, single and double stranded DNA and RNA, and the labeled conjugate probe comprises:
a labeling group conjugated to
a water-soluble polyglutaraldehyde prepared by polymerization at a pH of between 8 and 12 for up to about 48 hours, then acidifying to a pH of between 2 and 7, then separating the water-soluble polyglutaraldehyde from any water-insoluble polyglutaraldehyde,
and wherein the water-soluble polyglutaraldehyde is bound to a probe molecule selected from the group consisting of proteins, nucleic acids, carbohydrates, and lipids.

21. The method of claim 20 wherein the probe molecule specifically reacts with the target molecule by binding thereto.

22. The method of claim 21 wherein the probe molecule is first incubated with the water-soluble polyglutaraldehyde to form a conjugate which is then incubated with the labeling group to form the labeled conjugate probe.

23. The method of claim 22 wherein either or both incubations occur in the presence of a cationic detergent.

24. The method of claim 21 wherein the labeling group is first incubated with the water-soluble polyglutaraldehyde to form a labeled conjugate which is then incubated with the probe molecule to form the labeled conjugate probe.

25. The method of claim 24 wherein either or both incubations occur in the presence of a cationic detergent.

26. The method of claim 20 wherein the target molecule is viral nucleic acid.

27. The method of claim 20 further comprising removing unbound sample and detecting the labeled conjugate probe bound to the target molecule.

28. The method of claim 20 wherein the labeled conjugate probe is a labeled nucleic acid, comprising the additional step of mixing the probe with a hybridization medium prior to the step of reacting the probe with the target molecule.

29. The method of claim 20 wherein the target molecule is a double stranded nucleic acid molecule comprising the additional step of denaturing the target molecule with a denaturation medium prior to the step of reacting the target molecule with the labeled conjugate probe.

30. The method of claim 29 wherein a concentration of from 0.1 $\mu$g/ml to 50 $\mu$g/ml of labeled conjugate probe in a buffer solution is reacted with the denatured target molecule.

31. The method of claim 30 wherein the concentration of labeled conjugate probe is from 0.2 $\mu$g/ml to 30 $\mu$g/ml.

* * * * *